US010185139B2

(12) United States Patent
Nishijima

(10) Patent No.: US 10,185,139 B2
(45) Date of Patent: Jan. 22, 2019

(54) ENDOSCOPE

(71) Applicant: OLYMPUS CORPORATION, Tokyo (JP)

(72) Inventor: Yoshikazu Nishijima, Uenohara (JP)

(73) Assignee: OLYMPUS CORPORATION, Tokyo (JP)

(*) Notice: Subject to any disclaimer, the term of this patent is extended or adjusted under 35 U.S.C. 154(b) by 174 days.

(21) Appl. No.: 15/273,974

(22) Filed: Sep. 23, 2016

(65) Prior Publication Data
US 2017/0010457 A1 Jan. 12, 2017

Related U.S. Application Data

(63) Continuation of application No. PCT/JP2014/067699, filed on Jul. 2, 2014.

(30) Foreign Application Priority Data

Mar. 25, 2014 (JP) .................................. 2014-062215

(51) Int. Cl.
*A61B 1/00* (2006.01)
*G02B 23/24* (2006.01)
(Continued)

(52) U.S. Cl.
CPC ........ *G02B 23/2476* (2013.01); *A61B 1/0051* (2013.01); *A61B 1/0055* (2013.01); *A61B 1/0057* (2013.01); *F16L 13/103* (2013.01)

(58) Field of Classification Search
CPC . G02B 23/2476; A61B 1/0055; A61B 1/0057; A61B 1/0051; A61B 1/0052;
(Continued)

(56) References Cited

U.S. PATENT DOCUMENTS

2001/0023313 A1* 9/2001 Ide ..................... A61B 1/00137
600/142
2005/0131279 A1* 6/2005 Boulais .............. A61B 1/00059
600/141
(Continued)

FOREIGN PATENT DOCUMENTS

CN 101467865 A 7/2009
CN 101610709 A 12/2009
(Continued)

OTHER PUBLICATIONS

International Search Report dated Sep. 22, 2014 issued in PCT/JP2014/067699.

*Primary Examiner* — Timothy J Neal
(74) *Attorney, Agent, or Firm* — Scully, Scott, Murphy & Presser, P.C.

(57) ABSTRACT

An endoscope includes: a bending portion; a flexible tube portion provided on a proximal end side with respect to the bending portion; a plurality of bending wires inserted through the flexible tube portion and configured to bend the bending portion; a plurality of coil pipes through which the bending wires are respectively inserted; a connecting member provided on a distal end side of the flexible tube portion; and a coil pipe retaining member provided on a distal end side with respect to the connecting member, and including a plurality of holes for bending wires which respectively allow the bending wires to pass through, the coil pipe retaining member being configured to retain distal end portions of the plurality of coil pipes.

11 Claims, 5 Drawing Sheets

(51) Int. Cl.
*A61B 1/005* (2006.01)
*F16L 13/10* (2006.01)

(58) Field of Classification Search
CPC ... A61B 1/0053; A61B 1/0056; A61B 1/0058; F16L 13/103
See application file for complete search history.

(56) References Cited

U.S. PATENT DOCUMENTS

| | | |
|---|---|---|
| 2009/0171158 A1 | 7/2009 | Matsuo et al. |
| 2010/0004509 A1* | 1/2010 | Naito ............... A61B 1/0055 600/141 |
| 2010/0010309 A1 | 1/2010 | Kitagawa |

FOREIGN PATENT DOCUMENTS

| | | |
|---|---|---|
| EP | 2 127 591 A1 | 12/2009 |
| JP | 1-107301 U | 7/1989 |
| JP | 2007-298815 A | 11/2007 |
| JP | 2008-237812 A | 10/2008 |
| JP | 2009-153714 A | 7/2009 |
| JP | EP 2 074 926 A2 | 7/2009 |
| JP | 2010-17483 A | 1/2010 |
| WO | WO 2008/120422 A1 | 10/2008 |

\* cited by examiner

ENDOSCOPE

CROSS REFERENCE TO RELATED APPLICATION

This application is a continuation application of PCT/JP2014/067699 filed on Jul. 2, 2014 and claims benefit of Japanese Application No. 2014-062215 filed in Japan on Mar. 25, 2014, the entire contents of which are incorporated herein by this reference.

BACKGROUND OF THE INVENTION

1. Field of the Invention

The present invention relates to an endoscope, and more particularly to an endoscope having a flexible tube portion in which a plurality of bending wires for bending a bending portion are inserted.

2. Description of the Related Art

Conventionally, endoscopes have been widely used in industrial fields and medical fields. Some endoscopes have an elongated flexible insertion portion. The insertion portion includes, on the distal end side thereof, a bending portion, and the proximal end side of the bending portion is connected with a flexible tube portion. The bending portion is configured to be bendable by bending operation performed at the operation portion of the endoscope. The bending portion and the flexible tube portion are connected with a pipe sleeve, and the insertion portion including a connecting part with a pipe sleeve is covered with resin and the like.

Inside the flexible tube portion, at least two bending wires for bending the bending portion are inserted, and the operation portion provided at the proximal end portion of the flexible tube portion is operated to cause the bending wires to move forward or backward in the axial direction of the flexible tube portion, to thereby cause the bending portion to bend. The respective bending wires are inserted in coil pipes, and the plurality of coil pipes are provided in the flexible tube portion.

As disclosed in Japanese Patent Application Laid-Open Publication No. 2007-298815, the distal end portions of the bending wires are fixed to the bending piece in the bending portion, and the distal end portions of the coil pipes are fixed to the pipe sleeve that connects the bending portion and the flexible tube portion, by brazing or soldering.

SUMMARY OF THE INVENTION

According to one aspect of the present invention, it is possible to provide an endoscope including: a bending portion; a flexible tube portion provided on a proximal end side with respect to the bending portion; a plurality of bending wires for bending the bending portion, which are inserted in the flexible tube portion; a plurality of coil pipes through which the bending wires are respectively inserted; a pipe sleeve provided on a distal end side of the flexible tube portion; and a coil pipe retaining member provided on a distal end side with respect to the pipe sleeve, and including a plurality of holes for bending wires which respectively allow the bending wires to pass through, the coil pipe retaining member being configured to retain distal end portions of the plurality of coil pipes.

DETAILED DESCRIPTION OF THE PREFERRED EMBODIMENT

Figure 1:
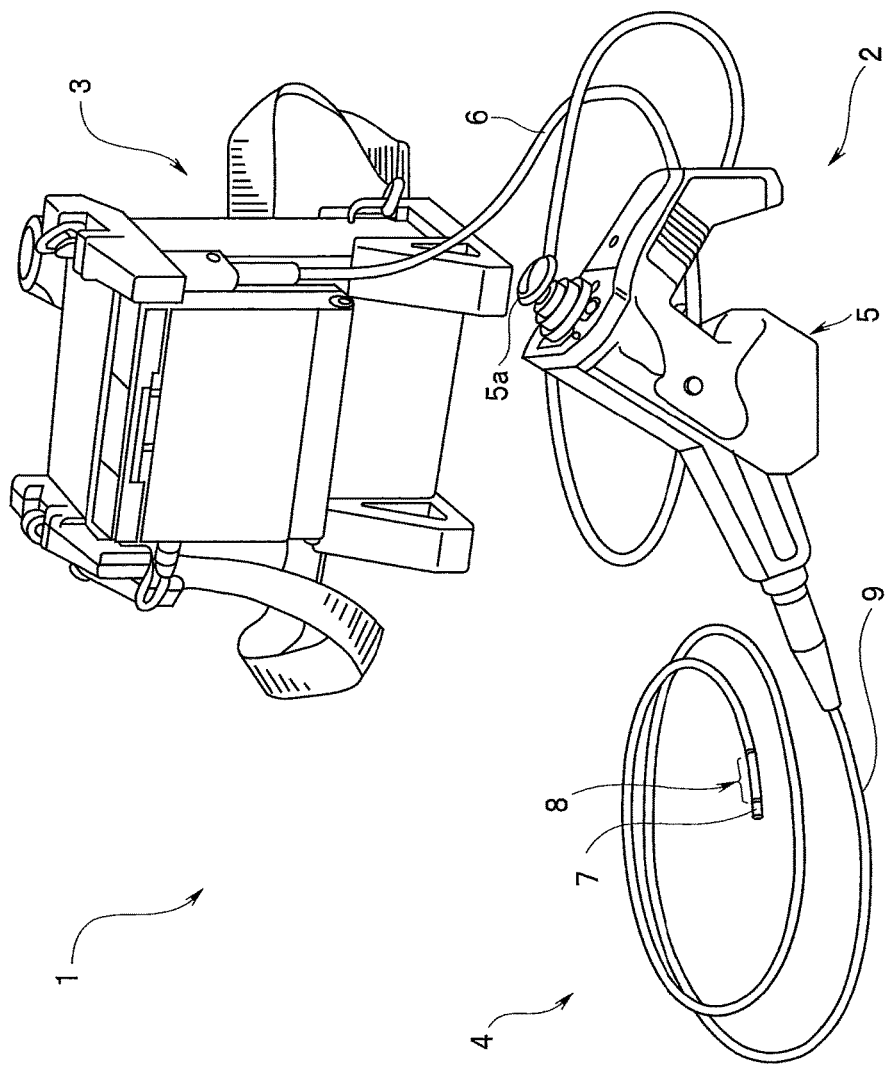
FIG. 1 is a configuration diagram showing a configuration of an endoscope system 1 according to the present embodiment.

Hereinafter, an embodiment of the present invention will be described with reference to drawings.

Note that, in the drawings used in the description below, a different scale size is used for each of the constituent elements in order to allow each of the constituent elements to be illustrated in a recognizable size in the drawings, and the present invention is not limited only to the number, shapes, ratio of the sizes of the constituent elements, and a relative positional relationship among the constituent elements shown in these drawings.

Configuration of Endoscope Apparatus

FIG. 1 is a configuration diagram showing a configuration of an endoscope system according to the present embodiment.

As shown in FIG. 1, an endoscope system 1 includes an endoscope 2 and an apparatus body 3 to which the endoscope 2 is connected.

The endoscope 2 is configured by including an elongated flexible insertion portion 4, an operation portion 5 connected to the proximal end portion of the insertion portion 4, and a universal cord 6 extended from the operation portion 5.

The insertion portion 4 includes continuously in the following order from the distal end side thereof, a distal end rigid portion 7, a bending portion 8, and a flexible tube portion 9 provided on the proximal end side with respect to the bending portion 8. The operation portion 5 is connected to the proximal end portion of the long flexible tube portion 9.

The bending portion 8 is bendable in four directions, i.e., up, down, left, and right directions, for example, by operating a joystick 5a provided at the operation portion 5. Note that the operation portion 5 is provided with not only the joystick 5a but also various kinds of switches, etc., for giving an instruction for photographing operation to be performed by an image pickup device (not shown) provided in the distal end rigid portion 7. Furthermore, an illumination section (not shown) using a light-emitting diode (LED) is provided in the distal end rigid portion 7.

The apparatus body 3 is box-shaped, for example, and includes on an external housing thereof a monitor for displaying an endoscopic image picked up by the endoscope 2.

Configuration of Connecting Part of Flexible Tube Portion and Bending Portion

Figure 2:
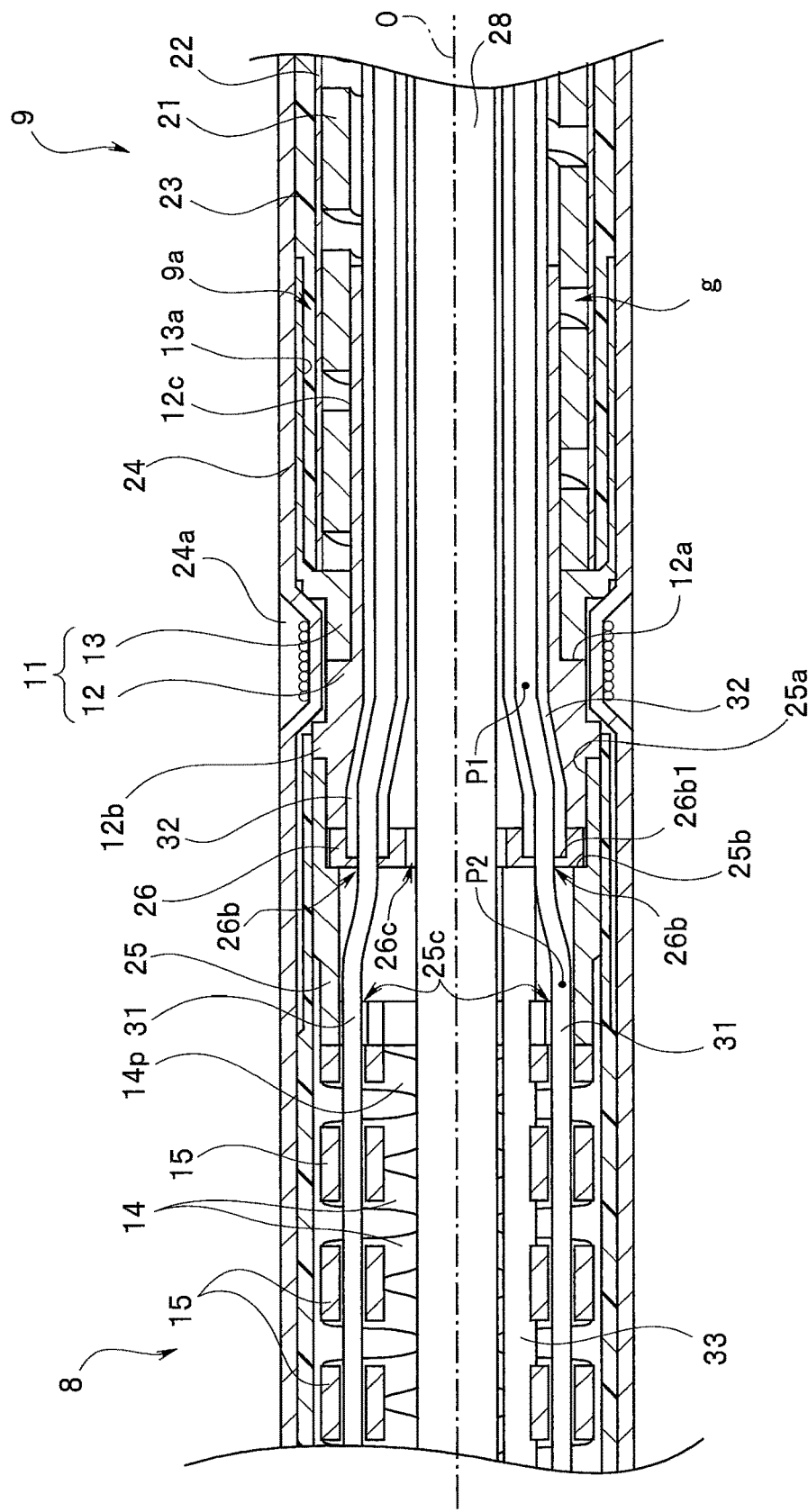
FIG. 2 is a cross-sectional view of a connecting part of a bending portion 8 and a flexible tube portion 9 according to the present embodiment.

FIG. 2 is a cross-sectional view of the connecting part of the bending portion 8 and the flexible tube portion 9 according to the present embodiment. The bending portion 8 and the flexible tube portion 9 are connected with the connecting member 11. The connecting member 11 is a cylindrical-shaped pipe sleeve provided on the distal end side of the flexible tube portion 9. The connecting member 11 is made of metal such as stainless steel.

The connecting member 11, which is a pipe sleeve, is configured by two cylindrical members 12 and 13. A step portion 12a is formed on the outer circumferential side of the cylindrical member 12, and the distal end portion of the cylindrical member 13 is externally fitted to the cylindrical member 12 from the proximal end portion of the cylindrical member 12 such that the distal end portion of the cylindrical member 13 abuts the step portion 12a. The cylindrical member 13 is connected and fixed to the cylindrical member 12 by laser welding applied to the step portion 12a. Note that the cylindrical members 12 and 13 may be fixed to each other by adhesive.

The bending portion 8 includes a plurality of bending pieces 14.

The proximal end parts of the cylindrical members 12 and 13 have a shape in which a gap g is formed between an outer circumferential surface 12c of the proximal end part of the cylindrical member 12 and an inner circumferential surface 13a of the proximal end part of the cylindrical member 13, when the distal end part of the cylindrical member 13 is externally fitted to the cylindrical member 12 from the proximal end side of the cylindrical member 12, and the cylindrical member 12 and the cylindrical member 13 are connected and fixed to each other.

The distal end thin wall portion 9a of the flexible tube portion 9 is arranged in the gap g in the state where the distal end thin wall portion 9a is sandwiched by the outer circumferential surface 12c of the proximal end side part of the cylindrical member 12 and the inner circumferential surface 13a of the proximal end side part of the cylindrical member 13.

The flexible tube portion 9 is configured by including a flex 21, a braid 22, and an outer sheath resin 23 which are layered in this order from the inner side. The flex 21 is a spiral tube which is a flexible member having a shape formed by winding a plate member in a spiral shape. The braid 22 is a metal braid. The outer sheath resin 23 is formed on the outer circumferential portion of the braid 22 such that a part of the outer sheath resin enters the fine clearances between the respective metal wires of the braid 22.

Furthermore, the insertion portion 4 is configured such that a braid 24 is provided from the distal end side to the proximal end side so as to cover the outer circumferences of the bending pieces 14, connecting member 11 and outer sheath resin 23. Note that the braid 24 may be an outer sheath resin.

On the outer circumferential portion of the connecting member 11, thread is wound around the outer circumferential portion of the braid 24, and adhesive 24a is applied on the thread.

As described above, the flexible tube portion 9 has a cylindrical-shaped flexible member, and the flexible member includes the flex 21, the outer sheath resin 23 that covers the flex 21, and a braid 22 provided between the flex 21 and the outer sheath resin 23.

The cylindrical-shaped joint receiving member 25 is connected to the distal end portion of the connecting member 11. The connecting member 11 and the joint receiving member 25 are connected and fixed to each other by welding or adhesive at the abutting part where the proximal end portion of the joint receiving member 25 and a projection portion 12b of the cylindrical member 12 abut against each other.

The joint receiving member 25 is connected to the proximal-most bending piece 14p such that the distal end portion of the joint receiving member 25 is internally fitted to the proximal-most bending piece 14p from the proximal end portion of the proximal-most bending piece 14p and the outer circumferential surface of the distal end portion of the joint receiving member 25 is fitted to the inner circumferential surface of the proximal-most bending piece 14p. That is, the joint receiving member 25 is a fixed member fixed to the proximal-most bending piece 14p of the bending portion 8.

The coil pipe retaining member 26 made of metal such as stainless steel, aluminum, brass, or the like is held in a sandwiched manner between the connecting member 11 and the joint receiving member 25. Note that the coil pipe retaining member 26 may be made of resin.

Specifically, the cylindrical-shaped joint receiving member 25 includes a circular step portion 25b formed in the circumferential direction on the inner circumferential surface 25a. The coil pipe retaining member 26 is inserted in the opening portion on the proximal end side of the joint receiving member 25, and then the distal end portion of the cylindrical member 12 is internally fitted in the opening portion on the proximal end side of the joint receiving member 25. The coil pipe retaining member 26 abuts the step portion 25b, and held in a sandwiched manner by the joint receiving member 25 and the cylindrical member 12. That is, the coil pipe retaining member 26 is held in the sandwiched manner by the connecting member 11 which is a pipe sleeve and the joint receiving member 25 which is a fixed member.

The four bending wires 31 are inserted respectively through the coil pipes 32. The distal ends of the four coil pipes 32 are retained at the coil pipe retaining member 26. The plurality of (four in the present embodiment) bending wires 31 are wires inserted in the flexible tube portion 9 and configured to bend the bending portion 8, and the bending wires 31 are inserted respectively through the plurality of (four in the present embodiment) coil pipes 32.

Configuration of Coil Pipe Retaining Member

Figure 3:
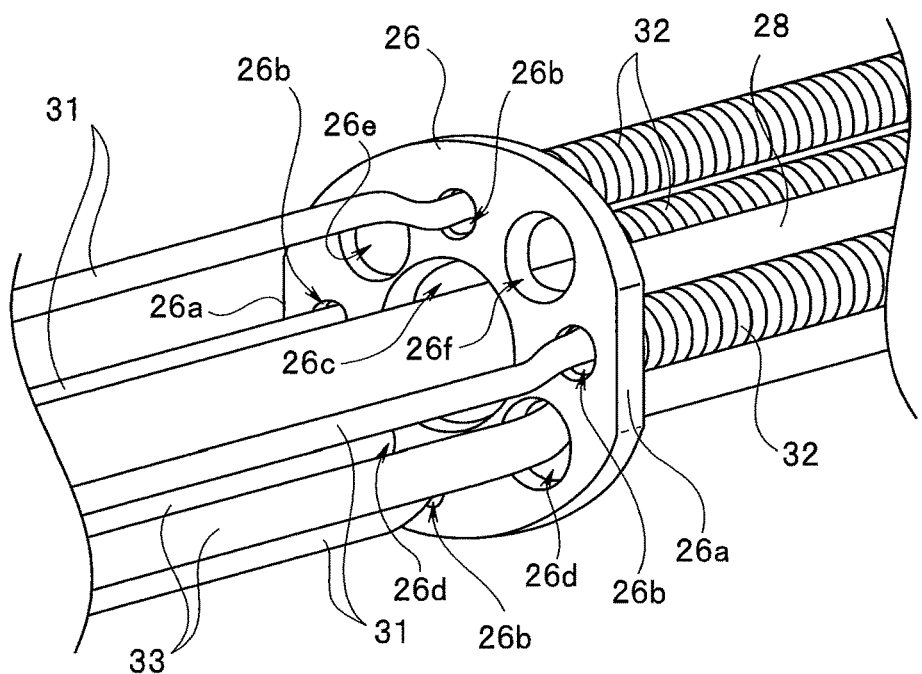
FIG. 3 is a perspective view of a coil pipe retaining member 26 to which distal end portions of four coil pipes are fixed and through which four bending wires 31, a signal cable 28, and two power source lines 33 are inserted, according to the present embodiment.
Figure 4:
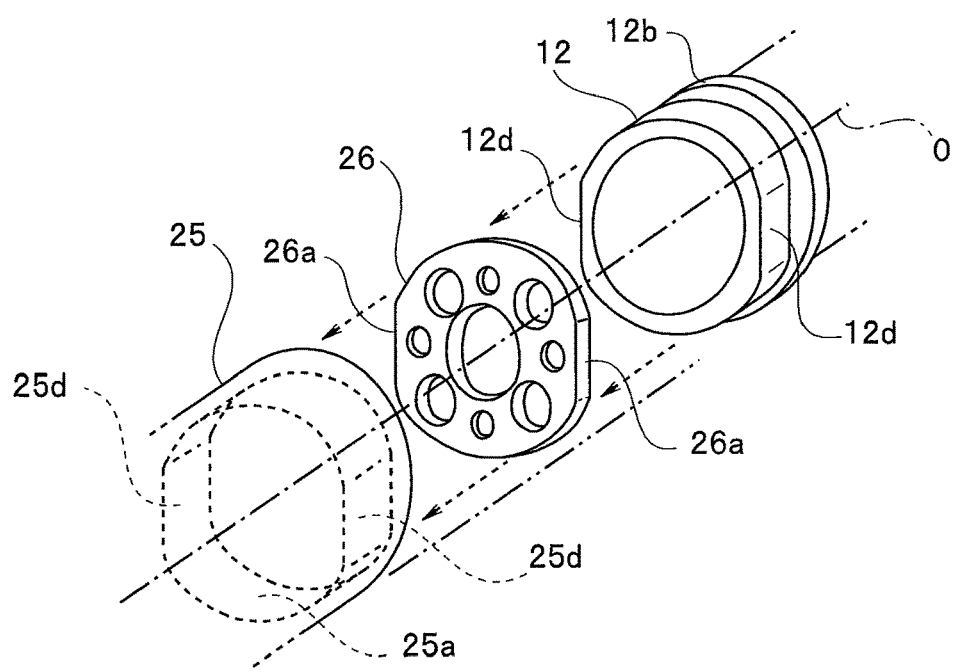
FIG. 4 is a schematic perspective view for illustrating a fitting relation among a joint receiving member 25, the coil pipe retaining member 26, and a connecting member 11, according to the present embodiment.

FIG. 3 is a perspective view of the coil pipe retaining member 26 to which the distal end portions of the four coil pipes are fixed and through which the four bending wires 31, a signal cable 28, and two power source lines 33 are inserted. FIG. 4 is a schematic perspective view for illustrating a fitting relation among the joint receiving member 25, the coil pipe retaining member 26, and the connecting member 11.

Figure 5:
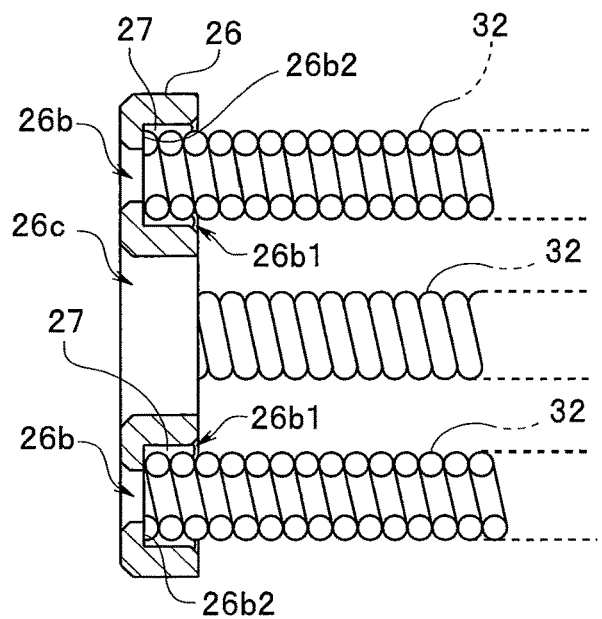
FIG. 5 is a cross-sectional view of the coil pipe retaining member 26 to which the distal end portions of the four coil pipes 32 are fixed, according to the present embodiment.

FIG. 5 is a cross-sectional view of the coil pipe retaining member 26 to which the distal end portions of the four coil pipes 32 are fixed.

As shown in FIG. 3, the coil pipe retaining member 26 is a disk-shaped member including cut portions 26a as positioning portions formed at two positions respectively, and includes a plurality of through holes. The two cut portions 26a are the parts for fixing the coil pipe retaining member 26 so as not to rotate around the axis with respect to the flexible tube portion 9. Note that the two cut portions 26a are formed on the coil pipe retaining member 26 in the present embodiment, but one cut portion may be provided.

Four holes 26b are the holes for the bending wires 31. The four holes 26b as the through holes are formed on the coil pipe retaining member 26 so as to be arranged at intervals of 90 degrees around the center axis of the circular coil pipe retaining member 26. Two cut portions 12d having a shape same as that of the cut portions 26a are formed also on the outer circumferential portion of the distal end portion of the cylindrical member 12.

On the inner circumferential surface 25a on which the step portion 25b of the joint receiving member 25 is formed, two plane portions 25d corresponding to the two cut portions 26a and the two cut portions 12d are formed. That is, the two plane portions 25d have a predetermined shape so as to fit to the two cut portions 26a and two cut portions 12d.

The coil pipe retaining member 26 and the cylindrical member 12 are inserted in the opening portion of the proximal end portion of the joint receiving member 25 such that the respective cut portions 26a and 12d closely contact the respective plane portions 25 on the inner circumferential surface 25a of the joint receiving member 25.

The respective cut portions 26a and 12d closely contact the respective plane portions 25d on the inner circumferential surface 25a, and thereby the positions of the coil pipe retaining member 26 and the cylindrical member 12 are determined so as not to move rotationally around the axis O of the flexible tube portion 9 in the opening portion of the proximal end portion of the joint receiving member 25.

Note that the parts having the predetermined shape which closely contact and fit to the respective cut portions 26a are formed on the joint receiving member 25 such that the respective cut portions 26a closely contact the respective plane portion 25d on the inner circumferential surface 25a of the joint receiving member 25. However, the parts having a predetermined shape which closely contact and fit to the cut portions 26a may be provided on the connecting member 11.

That is, the coil pipe retaining member 26 includes the cut portions 26a formed at two positions, as the positioning portions which abut at least one of the connecting member 11 and the joint receiving member 25 to fix the coil pipe retaining member so as not to rotate around the axis with respect to the flexible tube portion 9. The two cut portions 26a have the shape to be fitted to the predetermined shape of the parts formed on at least one of the connecting member 11 and the joint receiving member 25.

In addition, as shown in FIG. 5, the coil pipe retaining member 26 includes a plurality of recessed portions 26b1 and the distal end portions of the coil pipes 32 enter the recessed portions 26b1 to be retained at the recessed portions. The respective recessed portions 26b1 include the holes 26b for bending wires.

Each of the holes 26b has an inner diameter which allows each of the bending wires 31 to insert therethrough and which is smaller than the outer diameter of each of the coil pipes 32. The inner diameter of each of the recessed portions 26b1 is larger than the outer diameter of each of the coil pipes 32.

Therefore, each of the bending wires 31 inserted in each of the coil pipes 32 passes through the hole 26b, but the distal end portion of each of the coil pipes 32 is retained by a step portion 26b2 of each of the recessed portions 26b1. That is, the coil pipe retaining member 26 is arranged on the distal end side of the connecting member 11 as the pipe sleeve, and includes the plurality of holes 26b for bending wires which allow the bending wires 31 to respectively pass through, and configured to retain the distal end portions of the plurality of coil pipes 32.

The distal end portions of the coil pipes 32 are adhered and fixed respectively at the recessed portions 26b1 with adhesive 27.

Note that the distal end portions of the respective coil pipes 32 do not have to be fixed to the step portions 26b2 with the adhesive 27, and may be in the state engaged with the step portions 26b2. In the respective coil pipes 32, the bending wires 31 are inserted. Therefore, even if the distal end portions of the coil pipes 32 are detached from the holes 26b, the coil pipes do not largely get out of position in the direction perpendicular to the axis O in the insertion portion 4.

As shown in FIG. 2, the joint receiving member 25 includes holes 25c which respectively allow the four bending wires 31 to pass through. The bending wires 31 inserted through the respective holes 25c are inserted in the guide members 15 arranged and fixed in the bending pieces 14. The respective bending wires 31 are fixed to the distal-most bending piece, not shown.

As shown in FIG. 3, a center hole 26c of the coil pipe retaining member 26 is a hole through which the signal cable 28 of the image pickup device unit is inserted. Furthermore, two holes 26d for two power source lines 33 for LED illumination, a hole 26e for an air/water feeding pipe, and a hole 26f for a suction pipe are formed around the center hole 26c. Each of the four holes, i.e., the holes 26d, 26d, 26e, and 26f is provided between the adjacent two holes 26b for bending wires 31.

That is, the coil pipe retaining member 26 also includes a plurality of holes such as the hole 26c, etc., as the through holes through which internal components other than the plurality of coil pipes 32 inserted in the flexible tube portion 9 pass.

Note that the illumination section using an LED is provided in the distal end rigid portion 7 of the endoscope 2 in the present embodiment. However, if the illumination section using light guides including optical fibers is used, the light guides are respectively inserted through the two holes 26d.

Furthermore, if a heat radiation wire for dissipating the heat generated in the distal end rigid portion 7 to the proximal end side of the insertion portion is arranged in the flexible tube portion 9, the coil pipe retaining member 26 includes a hole for heat radiation wire for dissipating the heat generated in the distal end rigid portion 7 to the proximal end side of the insertion portion.

Working

According to the above-described configuration, the worker has only to insert the distal end portions of the respective coil pipes 32 in the recessed portions 26b1 as the retaining portions of the coil pipe retaining member 26 and fix the distal end portions in the recessed portions with the adhesive. Therefore, skilled technique is not required for the worker.

Furthermore, since the distal end portions of the coil pipes 32 are retained in the holes 26b of the coil pipe retaining member 26, the coil pipes 32 are not likely to move in the direction perpendicular to the axis O in the insertion portion 4 when the bending portion 8 is bent. Therefore, if the bending operation of the bending portion 8 is repeatedly performed, the coil pipes 32 are not likely to be entangled with each other or with other internal components. That is, the coil pipe retaining member 26 has the plurality of holes 26b, and has a function as a separator for separating the plurality of coil pipes 32 from each other at the connecting part of the bending portion 8 and the flexible tube portion 9.

According to the above-described embodiment, it is possible to provide an endoscope in which the distal end portions of the coil pipes inserted in the insertion portion can be fixed with a few man-hours without requiring skilled technique, and the coil pipes are not likely to be entangled with each other or with other internal components.

Next, modified examples will be described.

Modified Example 1

In the above-described embodiment, the four recessed portions 26b1 and the four holes 26b are formed on the coil pipe retaining member 26 such that the four coil pipes 32 are arranged in parallel with the axis O. However, the four recessed portions 26b1 and the four holes 26b may be formed on the coil pipe retaining member 26 such that the four coil pipes 32 are arranged not in parallel with the axis O, that is, the four coil pipes 32 have a predetermined angle α with respect to the axis O of the flexible tube portion 9.

Figure 6:
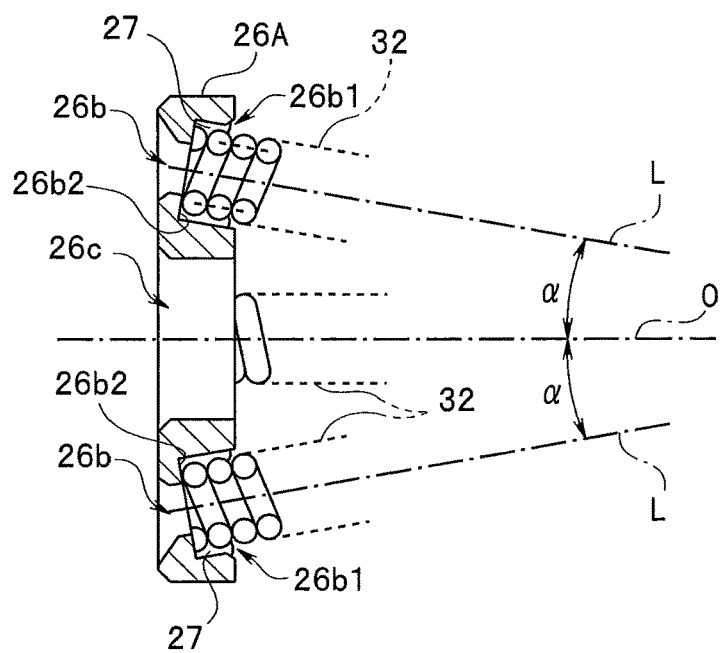
FIG. 6 is a cross-sectional view of a coil pipe retaining member 26A in which axes L of respective recessed portions 26b1 and respective holes 26b have a predetermined angle α with respect to an axis O of an insertion portion 4, according to a modified example 1 of the present embodiment.

FIG. 6 is a cross-sectional view of a coil pipe retaining member 26A in which the axes L of the respective recessed portions 26b1 and the respective holes 26b have the predetermined angle α with respect to the axis O of the insertion portion 4.

As shown in FIG. 2, inside the connecting part of the connecting member 11 and the joint receiving member 25, the bending wires 31 are extracted from the connecting member 11 through the position of the point P1 in the connecting member 11, and arranged so as to extend toward the position of the point P2 in the joint receiving member 25 via the coil pipe retaining member 26.

Therefore, in the present modified example, as shown in FIG. 6, the recessed portions 26b 1 and the respective holes 26b are formed on the coil pipe retaining member 26 such that the axes L of the respective recessed portions 26b1 and the respective holes 26b substantially coincide with the linear line extending from the position of the point P1 to the position of the point P2. That is, the recessed portions 26b1 and the holes 26b are formed such that the angle α formed by the axes L of the respective recessed portions 26b1 and the respective holes 26b with respect to the axis O of the flexible tube portion 9 substantially coincide with the angle formed by the segment connecting the point P1 and the point P2 with respect to the axis O of the flexible tube portion 9.

In other words, the coil pipes 32 are arranged so as to form the predetermined angle α with respect to the axis O of the flexible tube portion 9 from the connecting member 11 as the pipe sleeve to the holes 26b for bending wires. The holes 26b for bending wires are formed in accordance with the arrangement of the coil pipes 32.

According to such a configuration, the bending wires 31 are capable of moving forward or backward along the direction of the axis O with small friction resistance when passing through the holes 26b of the coil pipe retaining member 26 inside the connecting part of the connecting member 11 and the joint receiving member 25.

Modified Example 2

In the above-described embodiment and the modified example 1, the coil pipe retaining member 26 includes the step portion 26b2 on the inner circumferential side of each of the recessed portions 26b1 as shown in FIG. 5 and FIG. 6. However, the step portions 26b2 are not necessarily provided.

Figure 7:
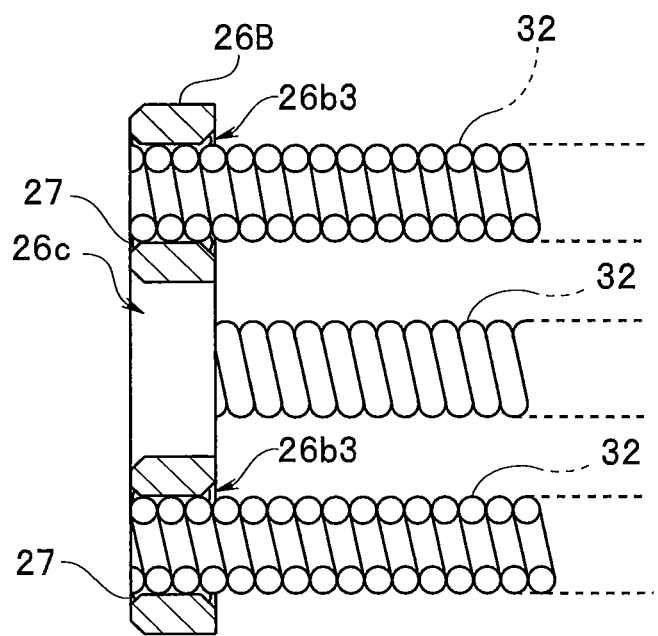
FIG. 7 is a cross-sectional view of a coil pipe retaining member 26B including only holes 26b3 without including step portions, according to a modified example 2 of the present embodiment.

FIG. 7 is a cross-sectional view of a coil pipe retaining member 26B including only holes 26b3 without including step portions.

As shown in FIG. 7, the distal end portions of the coil pipes 32 are fixed in the holes 26b3 with the adhesive 27. The inner diameter of each of the holes 26b3 is larger than the outer diameter of each of the coil pipes 32.

That is, the distal end portions of the coil pipes 32 are entered in the holes 26b3 for bending wires to be retained in the holes. Then, the distal end portions of the coil pipes 32 are adhered and fixed to the holes 26b3 for bending wires with the adhesive.

As described above, according to the above-described embodiment and modified examples, the worker does not have to be an expert to assemble the endoscope, which leads to not only the improvement of assembling property and reduction of man-hours but also prevention of occurrence of defective products and breakage.

In addition, it is possible to prevent the internal components from being entangled with each other, which leads to prevention of angle down, i.e., reduction of bending amount of the bending portion, and also leads to reduction of disconnection.

According to the above-described embodiment and modified examples, it is possible to provide an endoscope in which the distal end portions of the coil pipes inserted through the flexible tube portion can be fixed with a few man-hours and without skilled technique and the coil pipes are not likely to be entangled with each other or with other internal components in the flexible tube portion.

The present invention is not limited to the above-described embodiment and various changes, modifications, and the like are possible in a range without changing the gist of the present invention.

What is claimed is:

1. An endoscope comprising:
   an insertion section comprising:
      a bending portion; and
      a flexible tube portion provided proximally to the bending portion;
   a plurality of bending wires for bending the bending portion, the plurality of bending wires being inserted in the flexible tube portion;
   a plurality of coil pipes through which the bending wires are respectively inserted;
   a pipe sleeve provided at a distal end of the flexible tube portion;
   a coil pipe retaining member provided at a distal end of the pipe sleeve, the coil pipe retaining member including a first plurality of holes for the bending wires which respectively allow the bending wires to pass through, the coil pipe retaining member being configured to retain distal end portions of the plurality of coil pipes; and a fixed member fixed to a proximal-most bending piece in the bending portion,
wherein the coil pipe retaining member is held by being sandwiched between the pipe sleeve and the fixed member.

2. The endoscope according to claim 1, wherein the coil pipe retaining member includes a second plurality of holes which allow internal components inserted in the flexible tube portion to pass through, the internal components being other than the plurality of coil pipes.

3. The endoscope according to claim 1, wherein the coil pipe retaining member includes a positioning portion which abuts at least one of the pipe sleeve and the fixed member to fix the coil pipe retaining member so as not to rotate around an axis with respect to the flexible tube portion.

4. The endoscope according to claim 3, wherein the positioning portion of the coil pipe retaining member has a shape to be fitted to a predetermined shape of a part formed on at least one of the pipe sleeve and the fixed member.

5. The endoscope according to claim 1, further comprising
a plurality of recessed portions in which the distal end portions of the coil pipes are respectively entered and retained,
wherein the first plurality of holes for the bending wires are formed in the respective recessed portions.

6. The endoscope according to claim 5, wherein the distal end portions of the coil pipes are adhered and fixed to the recessed portions with adhesive.

7. The endoscope according to claim 1, wherein the distal end portions of the coil pipes are entered and retained in the first plurality of holes for the bending wires.

8. The endoscope according to claim 7, wherein the distal end portions of the coil pipes are adhered and fixed in the first plurality of holes for the bending wires with adhesive.

9. The endoscope according to claim 1, wherein
the coil pipes are arranged so as to have a predetermined angle with respect to an axis of the flexible tube portion from the pipe sleeve to the first plurality of holes for the bending wires, and
the first plurality of holes for the bending wires are formed in accordance with an arrangement of the coil pipes.

10. An endoscope comprising an insertion section comprising:
a bending portion; and
a flexible tube portion provided proximally to the bending portion;
a plurality of bending wires for bending the bending portion, the plurality of bending wires being inserted in the flexible tube portion;
a plurality of coil pipes through which the bending wires are respectively inserted;
a pipe sleeve provided at a distal end of the flexible tube portion;
a coil pipe retaining member provided at a distal end of the pipe sleeve, the coil pipe retaining member including a plurality of holes for the bending wires which respectively allow the bending wires to pass through, the coil pipe retaining member being configured to retain distal end portions of the plurality of coil pipes;
wherein the coil pipes are arranged so as to have a predetermined angle with respect to an axis of the flexible tube portion from the pipe sleeve to the plurality of holes for the bending wires, and
the plurality of holes for the bending wires are formed in accordance with an arrangement of the coil pipes.

11. An insertion section for use with an endoscope, the insertion section comprising:
a bending portion; and
a flexible tube portion provided proximally to the bending portion;
a plurality of bending wires for bending the bending portion, the plurality of bending wires being inserted in the flexible tube portion;
a plurality of coil pipes through which the bending wires are respectively inserted;
a pipe sleeve provided at a distal end of the flexible tube portion;
a coil pipe retaining member provided at a distal end of the pipe sleeve, the coil pipe retaining member including a plurality of holes for the bending wires which respectively allow the bending wires to pass through, the coil pipe retaining member being configured to retain distal end portions of the plurality of coil pipes; and
a fixed member fixed to a proximal-most bending piece in the bending portion,
wherein the coil pipe retaining member is held by being sandwiched between the pipe sleeve and the fixed member.

* * * * *